(12) United States Patent
Rovegno

(10) Patent No.: US 6,346,076 B1
(45) Date of Patent: Feb. 12, 2002

(54) ENDOSCOPE

(75) Inventor: Jean Rovegno, La Ciotat (FR)

(73) Assignee: Tokendo ( Sarl), La Ciotat (FR)

( * ) Notice: Subject to any disclaimer, the term of this patent is extended or adjusted under 35 U.S.C. 154(b) by 0 days.

(21) Appl. No.: 09/394,863

(22) Filed: Sep. 13, 1999

(30) Foreign Application Priority Data

Sep. 18, 1998 (FR) ............................................ 98 11826

(51) Int. Cl.$^7$ ................................................ A61B 1/00
(52) U.S. Cl. ...................... 600/173; 600/137; 600/163; 600/170
(58) Field of Search ................................ 600/137, 173, 600/130, 163, 167, 170; 356/241.1, 241.3; 359/367

(56) References Cited

U.S. PATENT DOCUMENTS

| | | | | |
|---|---|---|---|---|
| 2,118,523 A | * | 5/1938 | Pitman ........................ | 600/137 |
| 3,096,756 A | * | 7/1963 | Rosenfeld et al. .......... | 600/173 |
| 4,697,577 A | * | 10/1987 | Forkner ...................... | 600/173 |
| 5,575,757 A | * | 11/1996 | Kennedy et al. ............ | 600/167 |
| 5,797,836 A | * | 8/1998 | Lucey et al. ................ | 600/173 |

* cited by examiner

Primary Examiner—John P. Leubecker
(74) Attorney, Agent, or Firm—Greenblum & Bernstein, P.L.C.

(57) ABSTRACT

Rotary endoscope has a deflected distal sight. The endoscope includes a cylindrical handle. An endoscopic probe includes a distal optical deflector which introduces one-way inversion of an image of an object observed through a distal lateral lens port, a lens, and an optical image conveying system. The endoscopic probe has a proximal end which is accommodated in a distal part of the cylindrical handle, and is adapted to convey the image of the object observed along an optical axis to an ocular lens. An adjustment device moves the ocular lens in a controlled manner by an outer ring. The ocular lens is arranged in a median part of the cylindrical handle and is movable longitudinally along the optical axis. A one-way image rectifier is arranged in a proximal part of the cylindrical handle. The one-way image rectifier compensates for the one-way image inversion introduced by the distal optical deflector. A rotation device is movable in a controlled manner by an outer ring. The rotating device rotates, simultaneously and synchronously about the optical axis, each of the distal deflector and the one-way image rectifier. The proximal end of the endoscopic probe is coupled to the distal end of a cylindrical tube. Each of the endoscopic probe and the cylindrical tube is rotatable with respect to the cylindrical handle. The one-way image rectifier is arranged adjacent the proximal end of the cylindrical tube. The ocular lens is mounted in a cylindrical mount which is slidably and non-rotatably mounted in the median part of the cylindrical tube.

19 Claims, 2 Drawing Sheets

ENDOSCOPE

CROSS-REFERENCE TO RELATED APPLICATIONS

The present application claims priority under 35 U.S.C. §119 of French Patent Application No. 98 11826 filed on Sep. 18, 1998.

BACKGROUND OF THE INVENTION

1. Field of the Invention

The present invention relates to a rigid rotary endoscope with a deflected distal sight, and proximal adjustment. The technical field of the invention relates to endoscopy devices.

2. Discussion of Background Information

The term endoscope designates a rigid probe which, when it is introduced into an unlit cavity, allows the user to observe the interior of the cavity. For this purpose, an endoscope inherently incorporates an optical device and a lighting device.

The distal end of the optical device of an endoscope is disposed to the rear of an optical lens port, which is accommodated in the distal end of the endoscope. The proximal end of the optical device, which corresponds to an ocular lens, allows the user to observe the image of the area which is covered by the distal optical lens port. The optical device is calculated such that the image observed by the user does not have any either one-way or two-way inversion, relative to reality. An adjustment control ring, which is incorporated in the handle of the endoscope generally makes it possible to adjust the clarity of the image observed, by displacing the ocular lens longitudinally along the optical axis.

The distal end of the lighting device of an endoscope corresponds to a lighting window which is disposed at the distal end of the endoscope, and the lighting axis of which is parallel to the axis of sight of the distal optical lens port. The proximal end of the lighting device corresponds to a lighting base, which is incorporated in the handle of the endoscope. The distal lighting window lights the area which is covered by the distal optical lens port, when the lighting base is connected, by way of a lighting table, to a light generator.

The term axial sight endoscope designates an endoscope in which the optical axis of the distal optical lens port is combined with the mechanical shaft of the endoscope. The optical device of an endoscope with axial sight comprises a distal lens, an optical image conveying system, which generally consists of a series of achromatic lenses and an ocular lens. The optical device is calculated such that the image which is transmitted by the ocular lens does not have any two-way inversion relative to reality. The lighting device of an endoscope with axial sight consists of a bundle of lighting fibres, the proximal end of which corresponds to the lighting base, and the distal end of which generally constitutes a lighting window, in the form of a ring, which is disposed around the distal optical lens port.

The term deflected sight endoscope designates an endoscope in which the optical axis of the distal optical lens port forms an angle relative to the mechanical shaft of the endoscope. The sight is prograded if this angle is less than 90°, lateral if it is equivalent to 90°, and retrograde if it is greater than 90°. In all cases, the optical device of a deflected sight endoscope comprises a distal deflection prism which is disposed between the distal optical lens port and the lens of the optical device.

If the distal prism is a total reflection deflection prism, which is characterized by two-way inversion of the image transmitted by the prism, the optical device of the endoscope comprises the distal prism, a lens, an optical image conveying system, which generally consists of a series of achromatic lenses and an ocular lens. The optical image conveying system is calculated such that the image provided by the ocular lens is not totally inverted relative to reality. If the distal prism is a partial reflection deflection prism, characterized by one-way inversion of the image conveyed by the prism, the optical device of the endoscope comprises the distal prism, a lens, an optical image conveying system which generally consists of a series of achromatic lenses, a rectifier prism characterized by one-way inversion of the image conveyed by the prism, and an ocular lens, the radial positioning of the rectifier prism and the structure of the optical image conveying system being calculated such that the image provided by the ocular lens is not partially inverted relative to reality.

The lighting device of a deflected sight endoscope consists of a bundle of glass fibres, the proximal end of which is integrated in the lighting base of the endoscope, and the distal end of which constitutes a lateral lighting window, which is disposed between the optical lens port, and the distal end of the endoscope.

The difficulties in use which are inherent in conventional deflected sight endoscopes, relate to the panoramic exploration of the interior of a cavity. In fact, an examination of this type requires the user to make the endoscope rotate by 360° around its mechanical shaft, an operation which is made difficult by the presence of the lighting cable which is integral with the lighting base of the endoscope.

These problems in use have given rise to development of rotary endoscopes with deflected distal sight, designated by the manufacturers by the terms "Rotascope" (HENKE-SASS WOLFE), "Rotary shell endoscope" (EFER), "Rotary light connector boroscope" (KARL STORZ), "Rotary light connector technoscope" (RICHARD WOLF), or "Orbital scanning bore scope" (OLYMPUS). All these endoscopes have an endoscopic probe with deflected distal sight, the proximal end of which rotates inside a handle, which is provided with a ring, which controls the rotation of the sensor, a lateral lighting cable connection base, an adjustment ring, and a proximal viewing eye piece cup. This type of architecture allows the user to make the endoscopic probe rotate around its axis, without changing the position of the lighting cable, which is connected to the lateral lighting base of the endoscope. The optical devices which are used in the various above-described rotary endoscope models can be classified in one of the three families described hereinafter.

The first family of rotary endoscopes, which was developed many years ago, in particular by the German company HENKE-SASS WOLF, relates to endoscopes, the optical device of which, which is incorporated in the rotary endoscopic probe, consists of a distal deflector prism with total reflection, a lens, and an optical image conveying system. The image which is provided by the proximal end of the rotary endoscopic probe is transmitted to an ocular lens, which is accommodated in a sliding manner in the handle of the endoscope, and the longitudinal displacement of which is controlled by an adjustment ring. The main disadvantage of the above-described optical device is derived from the use of total reflection prisms which are relatively extensive, and difficult to produce in a large range of dimensions and deflection angles.

The second family of rotary endoscopes, which was developed many years ago, in particular by the French company EFER, relates to endoscopes, the optical device of which, which is integrated in the rotary endoscopic probe, consists of a distal deflection prism with partial reflection, a lens, and an optical image conveying system, inside which there is inserted a rectifier prism. The image which is provided by the proximal end of the rotary endoscopic sensor is transmitted to an ocular lens, which is accommodated in a sliding manner in the handle of the endoscope, and the longitudinal displacement of which is controlled by an adjustment ring. The main disadvantage of the above-described solution is derived from the fact that the small dimensions of the correction prism which is integrated in the rotary endoscopic probe, limit the global brightness of the endoscope, and in practice prevent use of an optical device of this type in endoscopic probes which have a small diameter.

The third family of rotary endoscopes relates to endoscopes, the optical device of which is integrated in the rotary endoscopic probe, consists of a distal deflection prism with partial reflection, a lens, and an optical image conveying system. The image provided by the proximal end of the optical image conveying system which is incorporated in the rotary endoscopic probe, is transmitted to an ocular lens, which is secured in the distal end of a mount accommodated in the handle of the endoscope, with which ocular lens there is associated a rectifier prism secured in the proximal end of the mount. The proximal end of the rotary endoscopic probe is mechanically associated with the mount, which contains the ocular lens and the rectifier prism, such that the distal deflection prism of the endoscopic probe, and the rectifier prism, maintain the same alignment during rotation of the probe around its axis. The above-described method provides for synchronising the rotation of a deflection prism with partial reflection, disposed at the distal end of an optical system, with that of a rectifier prism which is disposed at the proximal end of the optical system, has been described extensively in various patents relating to use of periscope systems (ERNST LEITZ GMBH / UK PATENT 1 272 742 / 1965, THEORDOR PREUSSNER / UK PATENT 2 187 303 A / 1987). In the case of a rotary endoscope with deflected distal sight, the device for correction of the direction of the image which consists of connecting in rotation the endoscopic probe and the mount which contains the ocular lens and the rectifier prism, must be associated with an adjustment device, which makes it possible to displace the mount longitudinally relative to the proximal end of the endoscopic probe.

The method which is public knowledge, and consists of associating the proximal end of a rotary endoscopic probe with a mount which contains a distal ocular lens and a proximal rectifier prism, was used before 1989, by the German company RICHARD WOLF. The architecture adopted by this manufacturer is characterized by the structure of the handle of these endoscopes, which has two mechanical parts connected in rotation, i.e., a distal part, which has a rotation control ring, and a lateral base for connection of the lighting cable, and a proximal part, which has an adjustment ring to control the longitudinal displacement of the mount which contains the ocular lens and the rectifier prism, which mount is accommodated in a sliding, but not rotary manner, inside the proximal part. The proximal end of the endoscopic probe, which rotates freely inside the distal part of the handle, is mechanically integral with the proximal part of the handle. The main disadvantage of the above-described solution is derived from the fact that the rotation of the endoscopic probe gives rise to rotation of the proximal part of the handle, and thus rotation of the eye piece cup of the endoscope, which is disposed in front of the eye of the user.

This disadvantage has been eliminated in rotary endoscopes with deflected distal sight, which have been marketed since 1995 by the Japanese company OLYMPUS, and described in the patents filed in 1993, by the English company KEYMED (UK PATENT GB 2 280 514 B, EUROPEAN PATENT EP 0 636 915 BI, US PATENT 5,540,650). These endoscopes are characterized by specific mechanical connection devices, provided in the mount, which contain the ocular lens and the rectifier prism, which mount is accommodated in a sliding and rotary manner inside the handle of the endoscopes.

A first connection device of a sliding nature, allows the proximal end of the endoscopic probe to transmit its movement of rotation to the mount which contains the ocular lens and the rectifier prism, irrespective of the longitudinal positioning of the mount in the handle. A second connection device allows the adjustment ring to displace longitudinally in the handle, the mount which contains the ocular lens and the rectifier prism, irrespective of the radial positioning of the mount in the handle. The main disadvantage of the above-described solution is derived from the mechanical tolerances required by the complex kinematic devices associated with the mount which contains the ocular lens and the rectifier prism, which tolerances give rise to:

variations of angular alignment between the distal deflection prism of the endoscopic probe, and the rectifier prism, which variations lead to random orientation faults of the image provided by the endoscope, and variations of centering of the rectifier prism on the optical axis of the endoscope, which variations lead to random angular deflections of the output axis of the image provided by the endoscope.

All of the above-described endoscopes also have the following disadvantages:

a range of rotation of the endoscopic probe which is less than 360°, and therefore does not allow the user to carry out a complete panoramic inspection of the area observed difficulties in adjusting the clarity of image, derived from an angular hysteresis of the adjustment ring, caused by the longitudinal mechanical play of the kinematic devices which are designed to displace the ocular lens longitudinally.

The object of the present invention is to describe a rotary endoscope with a deflected distal sight, and proximal adjustment, which does not have any of the above-described general or specific disadvantages, the technical concept and ergonomic characteristics of which endoscope are described in the following section, which provides a brief description of the invention.

SUMMARY OF THE INVENTION

The invention provides for a rotary endoscope with a deflected distal sight, the endoscope comprising a cylindrical handle, an endoscopic probe, comprising a distal optical deflector, which introduces one-way inversion of an image of an object observed through a distal lateral lens port, a lens, and an optical image conveying system, the proximal end of, which is accommodated in the distal part of the handle, conveys the image of the object observed along an optical axis to an ocular lens. An adjustment device is controlled by an outer ring which displaces longitudinally along the optical axis, the ocular lens, which is accommodated in the median part of the handle, A one-way image rectifier, which is accommodated in the proximal part of the handle, is positioned radially, such as to compensate for the one-way image inversion introduced by the distal deflector. A rotation device is controlled by an outer ring to rotate simultaneously and synchronously around the optical axis, the distal deflector, and the proximal rectifier. The endoscope is characterized in that the proximal end of the endoscopic probe is integral with the distal end of a cylindrical tube, which is accommodated such as to rotate in the cylindrical handle. The rectifier is integral in the proximal end of the cylindrical tube, and the ocular lens is secured in a cylindrical mount, which is accommodated such as to slide but not rotate, inside the median part of the cylindrical tube.

The rotation device may be controlled by an outer rotary ring, which is integral with the proximal part of the endoscopic probe, and surrounds the distal end of the distal part of the cylindrical handle, wherein rotation of the ring may entrain simultaneous rotation of the endoscopic probe and of the tube, which is accommodated in the handle. Rotation of the ring may thus entrain simultaneous rotation around the optical axis of the distal deflector of the endoscopic probe and of the rectifier, which is accommodated in the proximal end of the tube. The adjustment device may be controlled by a rotary outer ring, which surrounds the central part of the cylindrical handle. Rotation of the ring may entrain longitudinal displacement along the optical axis, of the cylindrical mount of the ocular lens, inside the cylindrical tube. A first mechanical connection device may transform movement of rotation of the outer adjustment ring, into longitudinal movement of translation of a ring, which surrounds the median part of the cylindrical tube. A second mechanical connection device may transform a movement of longitudinal translation of the ring around the median part of the cylindrical tube, into a movement of longitudinal translation of the cylindrical mount of the ocular lens inside the cylindrical tube. The connection device may be disposed such as to permit simultaneous rotation of the cylindrical tube and the mount of the ocular lens during use of the rotation device. The cylindrical mount of the ocular lens may have an outer, radial cylindrical finger, which slides in a longitudinal slot provided in the cylindrical tube. The ring which surrounds the median part of the cylindrical tube may have an inner annular groove, in which the end of the cylindrical finger can rotate freely. The ring also has a radial outer cylindrical finger, which slides in a longitudinal slot, which is provided in the central part of the cylindrical handle. The outer adjustment ring may have an inner helical thread with a square profile, in which there is accommodated the end of the cylindrical finger.

The cylindrical tube may have a mobile stop device which allows the endoscopic probe to carry out rotation greater than 360°. The cylindrical tube may be surrounded by an idle ring, which is positioned longitudinally between a proximal surface of a bearing, provided in the proximal end of the distal part of the cylindrical handle, and a distal surface of the bearing, which is provided in the distal end of the median part of the handle. The idle ring may have a radial slot, in the form of an arc of a circle, in which there is displaced a cylindrical radial finger which is integral with the cylindrical tube. The idle ring may have an outer cylindrical radial finger, which is disposed such as to abut a longitudinal finger, which is integral with the proximal surface of the bearing, which is provided in the distal part of the cylindrical handle. A cylindrical spring may be disposed around the cylindrical tube, between the proximal surface of the ring, which surrounds the median part of said cylindrical tube, and a distal surface of a bearing, which is provided in the proximal part of the handle. The distal deflector of the endoscopic probe may include a partial reflection prism. The optical image conveying system, may be accommodated in the endoscopic probe, and may convey to the ocular lens, the image of the object observed through the distal lateral lens port, and may include a plurality of achromatic lenses, which are disposed axially in an inner tube of the endoscopic probe. The rectifier may include an invertor prism.

The invention also provides for a rotary endoscope with a deflected distal sight, the endoscope comprising a cylindrical handle, an endoscopic probe comprising a distal optical deflector which introduces one-way inversion of an image of an object observed through a distal lateral lens port, a lens, and an optical image conveying system. The endoscopic probe has a proximal end which is accommodated in a distal part of the cylindrical handle, and is adapted to convey the image of the object observed along an optical axis to an ocular lens. An adjustment device moves the ocular lens in a controlled manner by an outer ring, the ocular lens being arranged in a median part of the cylindrical handle and being movable longitudinally along the optical axis. A one-way image rectifier arranged in a proximal part of the cylindrical handle, the one-way image rectifier compensating for the one-way image inversion introduced by the distal optical deflector, and a rotation device that is movable in a controlled manner by an outer ring, the rotating device rotating, simultaneously and synchronously about the optical axis, each of the distal deflector and the one-way image rectifier. The proximal end of the endoscopic probe is coupled to the distal end of a cylindrical tube, each of the endoscopic probe and the cylindrical tube being rotatable with respect to the cylindrical handle. The one-way image rectifier is arranged adjacent the proximal end of the cylindrical tube, and the ocular lens is mounted in a cylindrical mount which is slidably and non-rotatably mounted in the median part of the cylindrical tube.

The rotation device may be arranged on a distal part of the cylindrical handle. The adjustment device may surround the central part of the cylindrical handle and wherein a rotation of the adjustment device causes a longitudinal displacement along the optical axis of the cylindrical mount. The rotary endoscope may further comprise a first mechanical connection device for transforming rotation movement of the adjustment device into longitudinal movement of a ring that surrounds the median part of the cylindrical tube, and a second mechanical connection device for transforming a movement of longitudinal translation of the ring surrounding the median part of the cylindrical tube into a longitudinal translation of the cylindrical mount. The cylindrical mount may include an outer radial finger which slidably engages a longitudinal slot arranged on the cylindrical tube. The ring surrounding the median part of the cylindrical tube may comprise an inner annular groove which is adapted to receive a cylindrical finger. The rotary endoscope may further comprises at least one of the adjustment device comprising an inner helical thread which is adapted to engage a cylindrical finger, and the cylindrical tube including a mobile stop device which allows the endoscopic probe to rotate more than 360°.

The invention also contemplates a rotary endoscope with a deflected distal sight, the endoscope comprising a cylindrical handle having a proximal part, a median part and a distal part, an endoscopic probe comprising a lens, an optical image conveying system, a distal end, and a proximal end which extends from the distal end of the cylindrical handle. An optical deflector is arranged at the distal end of the endoscopic probe, the optical deflector introducing one-way inversion of an image of an object observed through a distal lateral lens port, the endoscopic probe conveying the image of the object observed along an optical axis to an ocular lens. An adjustment device comprises an outer ring which moves the ocular lens in a controlled manner, the ocular lens being disposed in a median part of the cylindrical handle and being movable longitudinally along the optical axis. A one-way image rectifier is arranged in the proximal part of the cylindrical handle, the one-way image rectifier compensating for the one-way image inversion introduced by the distal optical deflector, and a rotation device comprising an outer ring moving in a controlled manner, simultaneously and synchronously about the optical axis, each of the distal deflector and the one-way image rectifier. Each of the endoscopic probe and the cylindrical tube are rotatable with respect to the cylindrical handle, wherein the one-way image rectifier is arranged adjacent the proximal end of the cylindrical tube, and wherein the ocular lens is mounted in a cylindrical mount that is slidably and non-rotatably mounted in the median part of the cylindrical tube.

The endoscope provides for the following:

I. An endoscopic probe, the mechanical structure of which comprises an outer cylindrical tube, and an inner cylindrical tube. The probe incorporates an optical device, which comprises an optical lens port, which is disposed laterally in the distal end of the outer tube, a deflection prism with partial reflection, which is integral with the distal end of the inner tube, a lens, and an image conveying system, which are accommodated in the inner tube. The probe also includes a lighting device which is described in paragraph IV. The proximal end of the probe is accommodated in a rotary manner in the distal part of the handle described hereinafter in paragraph II. Selection of a deflection prism with partial reflection makes it possible to obtain economical prisms, which can be produced in a large range of dimensions and angles of deflection.

II. A cylindrical handle, the distal end of which is surrounded by a rotation control ring, is integral with the proximal part of the outer tube of the endoscopic probe, and the median part of which is surrounded by an adjustment ring. In addition, the handle has a lateral base for connection to a lighting cable, and an eye piece cup is integral with the proximal end of the handle. The handle does not have any external component, apart from the rotation control ring, which is integral with the rotation device described hereinafter in paragraph VI, and which, by way of untimely rotation movements, could distract the attention of the user.

III. A cylindrical tube has a distal end which is integral with the proximal end of the endoscopic probe. The tube is accommodated in a rotary manner inside the handle of the endoscope.

IV. A lighting device comprises a bundle of optical fibers, the individual fibers of which pass through the annular volume contained between the inner tube and the outer tube of the endoscopic probe. The distal end of the bundle of fibers is accommodated in a lateral lighting window, which is provided in the distal end of the outer tube of the endoscopic probe. The proximal part of the bundle of fibers leads inside the handle, through an aperture which is provided in the cylindrical tube, which is integral with the proximal end of the endoscopic probe. The proximal end of the bundle of fibers is accommodated in the end of the lateral lighting base of the handle. The proximal part of the bundle of fibers is coiled inside the handle, in order to prevent rotation of the probe from giving rise to forces which can break the fibers of the bundle.

V. An image rectifying device, utilizes a rectifying prism which is accommodated integrally in the proximal end of the cylindrical tube, which is integral with the proximal end of the endoscopic probe. This solution permits integration of a large-sized rectifier prism, which does not detract from the global brightness of the endoscope. This solution also makes it possible to ensure accurate, permanent angular alignment of the deflection prism, which is accommodated in the distal end of the probe, and of the rectifier prism which is securely accommodated in the proximal end of the cylindrical tube which is integral with the probe, as well as accurate, permanent centering of the rectifier prism on the optical axis of the endoscope.

VI. A rotation device, which is controlled by the control ring surrounds the distal end of the handle, and makes it possible to rotate inside the handle the proximal end of the endoscopic probe, as well as the cylindrical tube which is integral with the probe. The device is disposed such that there is no interaction with the adjustment device described hereinafter in paragraph VII.

VII. An adjustment device, which makes it possible to displace longitudinally the cylindrical mount of an ocular lens, is accommodated such as to slide but not rotate, inside the cylindrical tube, which is integral with the proximal end of the endoscopic probe. The device comprises a radial finger, which is integral with the mount of the ocular lens, and moves in a sliding manner in a longitudinal slot which is provided in the cylindrical tube, and the end of which moves in a rotary manner in an inner annular groove, which is provided in an idle ring, which surrounds the tube. The idle ring has an outer radial finger, which moves in a sliding manner in a longitudinal slot provided in the cylindrical handle, and the end of which is accomodated in the inner helical thread with a square profile, which is machined in the adjustment ring, which surrounds the cylindrical handle. The device is disposed such that there is no interaction with the rotation device previously described in paragraph VI.

VIII. A mobile stop device, makes it possible to rotate around more than 360° inside the handle, the proximal end of the endoscopic probe, as well as the cylindrical tube with which it is integral. The device comprises a radial finger, which is integral with the cylindrical tube, and moves in a radial slot, in the form of an arc of a circle, which is provided in an idle ring, which surrounds the tube. The ring has a radial finger which abuts a fixed finger which is integral with the handle. The device allows the user to carry out complete panoramic observation of the area observed.

IX. A device to eliminate longitudinal play, utilizes a helical spring, which surrounds the proximal end of the cylindrical tube, which is integral with the proximal end of the endoscopic probe, the spring being compressed between the proximal end of the handle, and the proximal surface of the ring, which is associated with the mount of the ocular lens, and surrounds the cylindrical tube. The device makes it possible to eliminate the fault of annular hysteresis caused by the adjustment control ring, and derived from the longitudinal play of the adjustment device.

BRIEF DESCRIPTION OF THE DRAWINGS

FIG. I illustrates the operating principle of the kinematic devices used in the rotary endoscope with a deflected distal sight, and proximal adjustment of the present invention; and FIG. II illustrates the structure of the rotary endoscope with a deflected distal sight, and proximal adjustment of the present invention.

DETAILED DESCRIPTION OF THE INVENTION

Figure 1:
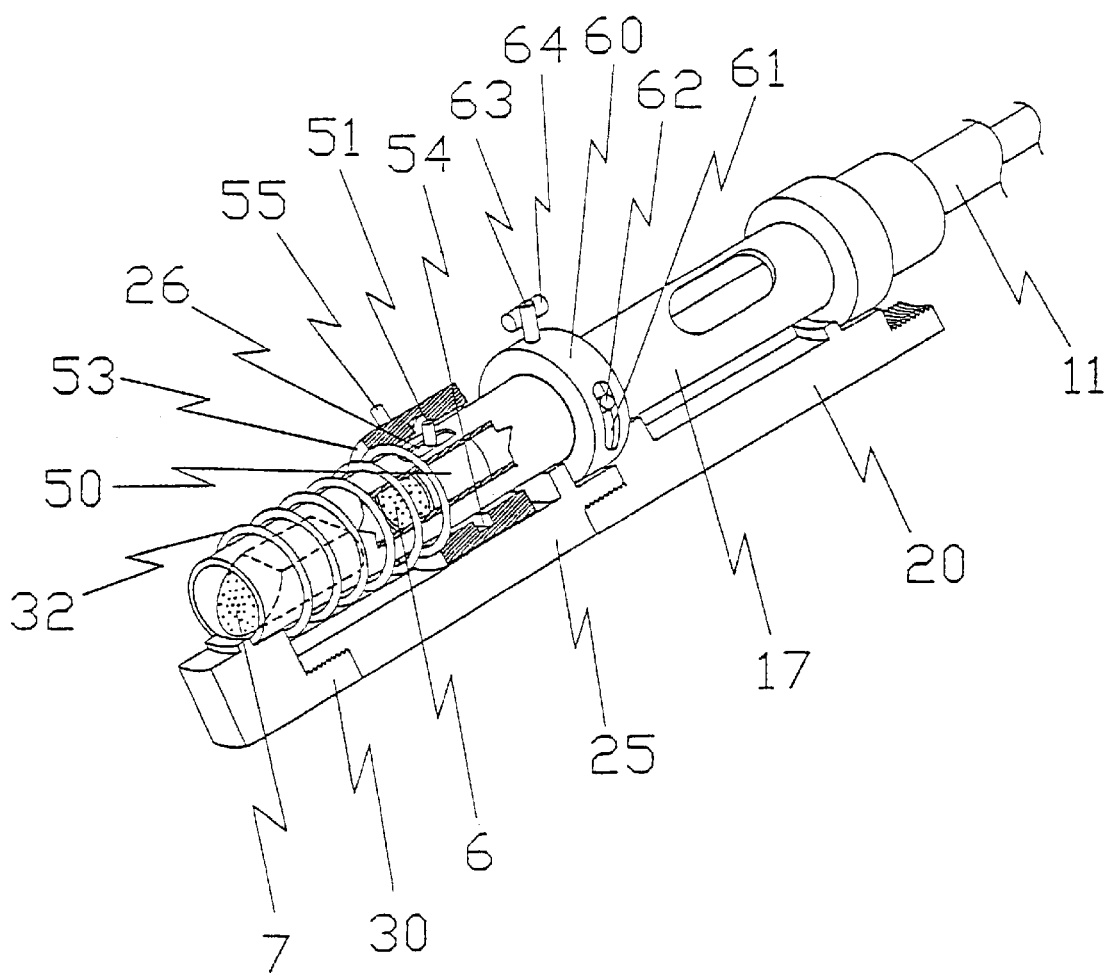
Figure 2:
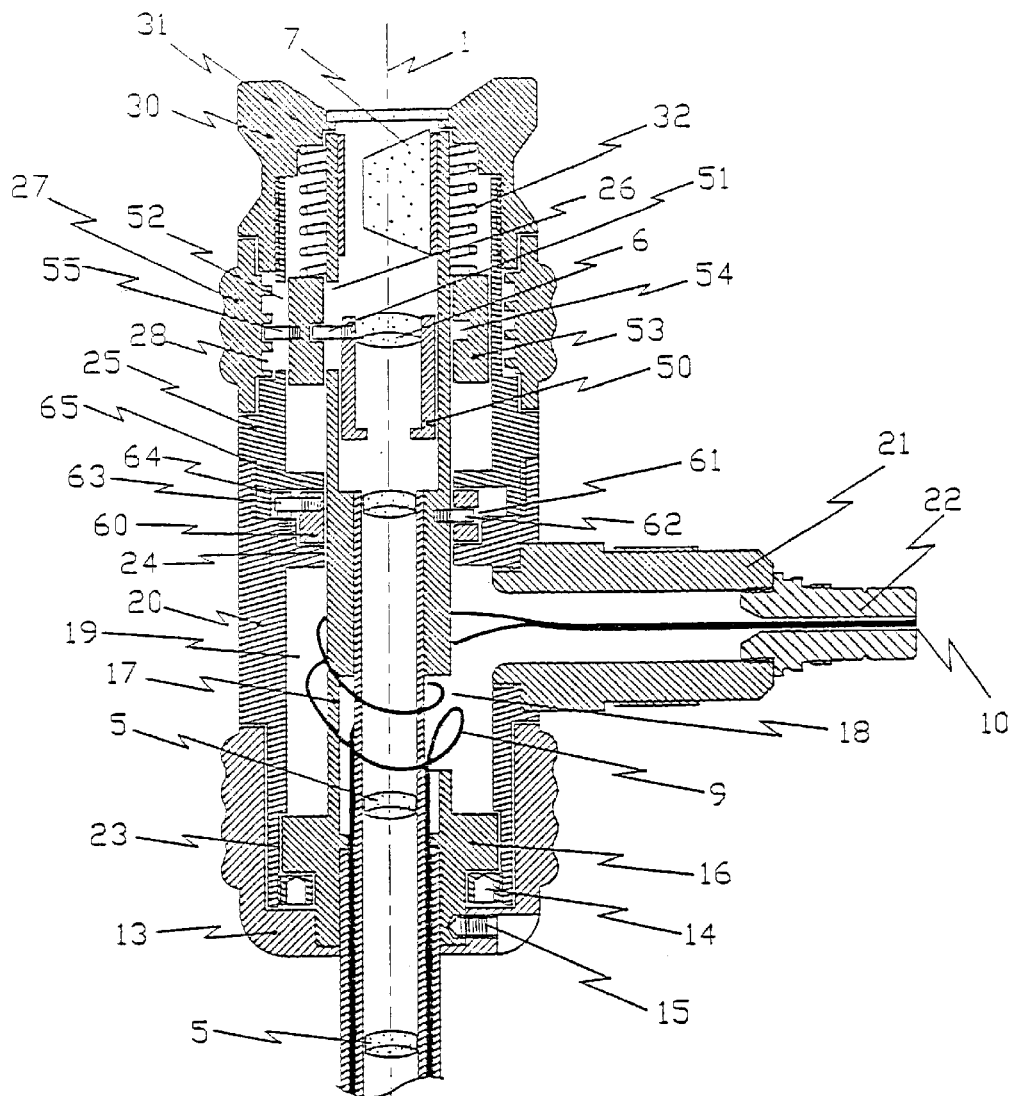
Figure 2:
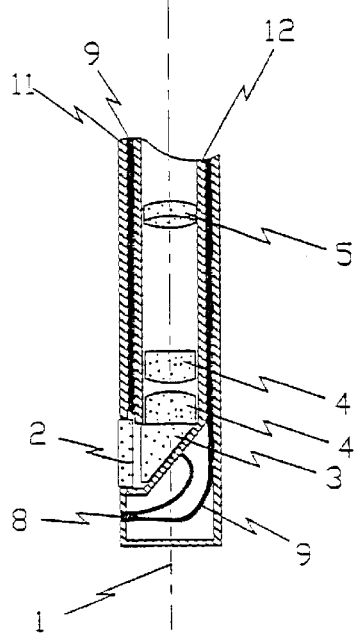

FIG. I illustrates the operating principles of the kinematic devices used in the rotary endoscope with a deflected distal sight, and proximal adjustment of the present invention. Rotation around its axis of the endoscopic probe with a deflected distal sight, which is accommodated in the outer cylindrical tube 11, gives rise to rotation inside the cylindrical handle 20, 25, 30 of the cylindrical tube 17, the distal end of which is integral with the proximal end of the tube 11, and the proximal end of which acts as a recess for an image rectifier, which utilizes for example an invertor prism 7.

A cylindrical mount 50, which acts as a recess for an ocular lens 6, is accommodated such as to slide but not rotate in the tube 17, has an outer radial cylindrical finger 51, which moves in a sliding manner in a longitudinal slot 26, which is provided in the tube 17. The end of the finger 51 is accommodated in a circulating manner in an inner annular groove 54 which is provided in an idle ring 53, which surrounds the tube 17. The ring 53 has an outer radial cylindrical finger 55, the longitudinal displacement of which, is controlled by the adjustment device described hereinafter in the text relative to FIG. II, makes it possible to regulate the clarity of the image conveyed by the ocular lens 6.

The tube 17 has an outer radial cylindrical finger 62, which is accommodated in a circulating manner in a radial slot 61, in the form of an arc of a circle, provided in an idle ring 60, which surrounds the tube 17. The ring 60 is accommodated between the proximal face of a shoulder which is provided in the proximal end of the distal component 20 of the handle 20, 25, 30, and the distal surface of a shoulder which is provided in the distal end of the central component 25 of the handle. The ring 60 has an outer radial finger 63, which abuts a longitudinal finger 64, which is integral with the proximal surface of the distal component 20 of the handle 20, 25, 30.

A helical spring 32, which surrounds the proximal end of the cylindrical tube 17, is compressed between the proximal surface of the ring 53, and the distal surface of a bearing which is provided in the proximal end of the proximal component 30 of the handle 20, 25, 30.

FIG. II illustrates the structure of the rotary endoscope with a deflected distal sight, and proximal adjustment of the present invention, the arrangement of which is described hereinafter.

The mechanical structure of the endoscopic probe is organized around an inner metal tube 12, and an outer metal tube 11. The optical system which is integrated in the endoscopic probe, comprises an optical lens port 2, disposed laterally in the distal end of the tube 11, an optical deflector, which for example utilizes a deflection prism 3, with partial reflection, which is integral with the distal end of the tube 12, and introduces one-way inversion of the image of the object observed through the lens port 2, a distal lens, which is accommodated in the tube 12, and utilizes for example two lenses 4, and an optical image conveying system, which for example includes a series of achromatic lenses 5, disposed axially in the tube 12, and conveyed to the ocular lens 6 the image of the object observed through the distal lateral lens port 2.

The proximal end of the outer tube 11 is surrounded integrally by a hub 16 which rotates freely inside a bearing 23, which is provided in the distal part of the distal component 20 of the cylindrical handle 20, 25, 30. A ring 14, which has an outer thread, and surrounds the distal part of the hub 16, is screwed into the distal end of the distal component 20 of the handle, in order to keep the hub in place in the handle. The proximal end of the hub 16 is integral with a cylindrical tube 17, which rotates freely inside a bearing 24, which is provided in the proximal end of the distal component of the handle 20, 25, 30, inside a bearing 65, provided in the distal end of the central component 25 of the handle, as well as inside a bearing 31, which is provided in the proximal end of the proximal component 30 of the handle. The proximal part of the inner tube 12 of the endoscopic probe in which there are accommodated the achromatic lenses 5 of the image conveying optical system, is accommodated inside the tube 17, such that the proximal end of the tube 12 is positioned in the central part of the tube 17.

The image rectifier, which for example utilizes an invertor prism 7, is integral in the proximal end of the cylindrical tube 17, and is positioned radially in the tube, such as to compensate for the one-way image inversion introduced by the distal deflection prism 3. The ocular lens 6 is integral in a cylindrical mount 50, the mount being accommodated such as to slide but not rotate, inside the cylindrical tube 17, between the distal end of the rectifier prism 7, and the proximal end of the optical image conveying system of the endoscopic probe. The cylindrical mount 50 has an outer radial cylindrical finger 51, which slides in a longitudinal slot 26, which is provided in the cylindrical tube 17. An idle ring 53, which surrounds the cylindrical tube 17, has an inner annular groove 54 with a square profile, in which the end of the cylindrical finger 51 can move freely, thus allowing the tube 17 to rotate freely inside the ring 53, irrespective of the longitudinal positioning of the mount 50 in the tube.

The lighting system, which is incorporated in the endoscope, comprises a bundle 9 of optical fibers, the individual fibers of which pass into the annular volume between the inner tube 12 and the outer tube 11 of the endoscopic probe. The distal end of the bundle of fibers 9 is glued, then polished, in the lateral lighting window 8, which is provided in the distal end of the outer tube 11 of the endoscopic probe. The proximal part of the bundle of fibers 9 ends in the volume 19, which is disposed inside the distal end 20 of the handle 20, 25, 30, through a window 18, which is provided in the proximal part of the cylindrical tube 17, between the proximal surface of the part 16, and the distal surface of the bearing 24. The proximal end of the bundle of fibers 9 is glued, then polished, in the lighting joining piece 22, which is secured to the end of the lateral base 21, which is integral with the distal component 20 of the handle 20, 25, 30. Several coils of the bundle of fibers are wound around the tube 17 inside the volume 19, which is provided inside the distal component 20 of the handle 20, 25, 30, in order to prevent rotation around 360° of the endoscopic probe from giving rise to mechanical stresses which are dangerous for the bundle of fibers.

The device for rotation of the endoscopic probe around its optical axis 1 is actuated by an outer rotary ring 13, which is integral with the proximal part of the endoscopic probe 11, and surrounds the distal end of the distal component 20 of the cylindrical handle 20, 25, 30, the control ring being secured integrally with the distal end of the hub 16, by way of a screw 15. Rotation of the ring 13 thus gives rise to rotation of the cylindrical tube 17 inside the handle 20, 25, 30, and thus simultaneous rotation around the optical axis 1 of the distal deflection prism 3, and of the rectifier prism 7.

The device for adjustment of the endoscope is controlled by an outer ring 27, which surrounds the proximal part of the central component 25 of the handle 20, 25, 30, and has an inner helical thread with a square profile, in which there is accommodated and entrained, the end of a radial cylindrical finger 55, which is integral with the ring 53, and is accommodated in a sliding manner in a longitudinal slot 52, provided in the proximal part of the central component 25 of the handle. The connection device which is thus formed, makes it possible to displace longitudinally along the optical axis 1, the mount 50, inside the tube 17, irrespective of the radial positioning of the tube. The connection device also allows the cylindrical tube 17, and thus the mount 50 of the ocular lens 6, to rotate freely inside the ring 53, during use of the rotation device of the endoscope, which is controlled by the outer ring 13.

The mobile stop device which limits the range of rotation of the cylindrical tube 17 inside the handle 20, 25, 30, is organized around an idle ring 60, which surrounds the tube, and is positioned between the proximal surface of the bearing 24, which is machined in the proximal end of the distal component 20 of the handle, and the distal surface of the bearing 65, which is machined in the distal end of the central component 25 of the handle. The ring 60 has a radial slot 61 in the form of an arc of a circle, which acts as a recess for a radial cylindrical finger 62, which is integral with the tube 17. The ring 60 also has an outer cylindrical radial finger 63, which is disposed such as to abut a longitudinal finger 64, which is integral with the proximal surface of the distal component 20 of the handle 20, 25, 30.

The mechanism for adjustment of the endoscope is associated with a device to eliminate longitudinal play, utilizes a helical spring 32, which surrounds the proximal end of the cylindrical tube 17, which end is disposed inside the proximal component 30 of the cylindrical handle 20, 25, 30. The distal end of the spring abuts the proximal surface of the ring 53 which surrounds the tube 17, whereas its proximal end is thwarted on the proximal surface of the bearing 31, which is provided in the proximal end of the proximal component 30 of the handle 20, 25, 30. The device to eliminate the play makes it possible to eliminate the angular hysteresis fault which is derived from the mechanical play, which inherently exists between the lateral surfaces of the helical thread 28, and the outer surface of the cylindrical finger 55, which is accommodated in a circulating manner in the thread.

It will be appreciated that the applications of the rotary endoscopes with a deflected sight, and adjustment, which form the present invention can be both medical and industrial.

It will also be appreciated, as can be understood from the foregoing description, that the present invention is not limited in any way to the methods of implementation, embodiments or applications which have been described explicitly. On the contrary, the present invention incorporates all variants which can be conceived by persons skilled in the art, without departing from the context of the present invention.

What is claimed is:

1. A rotary endoscope with a deflected distal sight, the endoscope comprising:
   a cylindrical handle;
   an endoscopic probe, comprising a distal optical deflector, which introduces one-way inversion of an image of an object observed through a distal lateral lens port, a lens, and an optical image conveying system, the proximal end of which, accommodated in the distal part of the handle, conveys the image of the object observed along an optical axis to an ocular lens;
   an adjustment device controlled by an outer ring displaces longitudinally along the optical axis, the ocular lens, which is accommodated in the median part of the handle;
   a one-way image rectifier accommodated in the proximal part of the handle, and positioned radially, such as to compensate for the one-way image inversion introduced by the distal deflector;
   a rotation device controlled by an outer ring rotates simultaneously and synchronously around the optical axis, the distal deflector, and the proximal rectifier;
   the endoscope being characterized in that:
      the proximal end of the endoscopic probe is integral with the distal end of a cylindrical tube, which is accommodated such as to rotate in the cylindrical handle;
      the rectifier is integral in the proximal end of the cylindrical tube; and
      the ocular lens is secured in a cylindrical mount, which is accommodated such as to slide but not rotate, inside the median part of the cylindrical tube.

2. A rotary endoscope according to claim 1, characterized in that:
   the rotation device is controlled by an outer rotary ring, which is integral with the proximal part of the endoscopic probe, and surrounds the distal end of the distal part of the cylindrical handle;
   wherein rotation of the ring entrains simultaneous rotation of the endoscopic probe and of the tube, which is accommodated in the handle; and
   wherein rotation of the ring thus entrains simultaneous rotation around the optical axis of the distal deflector of the endoscopic probe and of the rectifier, which is accommodated in the proximal end of the tube.

3. A rotary endoscope according to claim 2, characterized in that:
   the adjustment device is controlled by a rotary outer ring, which surrounds the central part of the cylindrical handle;
   rotation of the ring entrains longitudinal displacement along the optical axis, of the cylindrical mount of the ocular lens, inside the cylindrical tube.

4. A rotary endoscope according to claim 3, characterized in that:
   a first mechanical connection device transforms movement of rotation of the outer adjustment ring, into longitudinal movement of translation of a ring, which surrounds the median part of the cylindrical tube;
   a second mechanical connection device transforms a movement of longitudinal translation of the ring around the median part of the cylindrical tube, into a movement of longitudinal translation of the cylindrical mount of the ocular lens inside the cylindrical tube;
   the connection devices being disposed such as to permit simultaneous rotation of the cylindrical tube and the mount of the ocular lens during use of the rotation device.

5. A rotary endoscope according to claim 4, characterized in that:
   the cylindrical mount of the ocular lens has an outer, radial cylindrical finger, which slides in a longitudinal slot provided in the cylindrical tube;
   the ring which surrounds the median part of the cylindrical tube has an inner annular groove, in which the end of the cylindrical finger can rotate freely; the ring also having a radial outer cylindrical finger, which slides in a longitudinal slot, which is provided in the central part of the cylindrical handle;

the outer adjustment ring has an inner helical thread with a square profile, in which there is accommodated the end of the cylindrical finger.

6. A rotary endoscope according to claim 1, characterized in that:

the cylindrical tube has a mobile stop device which allows the endoscopic probe to carry out a rotation greater than 360°.

7. A rotary endoscope according to claim 6, characterized in that:

the cylindrical tube is surrounded by an idle ring, which is positioned longitudinally between a proximal surface of a bearing, provided in the proximal end of the distal part of the cylindrical handle, and a distal surface of the bearing, which is provided in the distal end of the median part of the handle;

the idle ring has a radial slot, in the form of an arc of a circle, in which there is displaced a cylindrical radial finger integral with the cylindrical tube;

the idle ring has an outer cylindrical radial finger disposed such as to abut a longitudinal finger, which is integral with the proximal surface of the bearing, and provided in the distal part of the cylindrical handle.

8. A rotary endoscope according to claim 1, characterized in that:

a cylindrical spring is disposed around the cylindrical tube, between the proximal surface of the ring, which surrounds the median part of said cylindrical tube, and a distal surface of a bearing, which is provided in the proximal part of the handle.

9. A rotary endoscope according to claim 1, characterized in that:

the distal deflector of the endoscopic probe includes a partial reflection prism.

10. A rotary endoscope according to claim 1, characterized in that:

the optical image conveying system, which is accommodated in the endoscopic probe, and conveys to the ocular lens, the image of the object observed through the distal lateral lens port, includes a plurality of achromatic lenses, which are disposed axially in an inner tube of the endoscopic probe.

11. A rotary endoscope according to claim 1, characterized in that:

the rectifier includes an invertor prism.

12. A rotary endoscope with a deflected distal sight, the endoscope comprising:

a cylindrical handle;

an endoscopic probe comprising a distal optical deflector which introduces one-way inversion of an image of an object observed through a distal lateral lens port, a lens, and an optical image conveying system, the endoscopic probe having a proximal end which is accommodated in a distal part of the cylindrical handle, and being adapted to convey the image of the object observed along an optical axis to an ocular lens;

an adjustment device which moves the ocular lens in a controlled manner by an outer ring, the ocular lens being arranged in a median part of the cylindrical handle and being movable longitudinally along the optical axis;

a one-way image rectifier arranged in a proximal part of the cylindrical handle, the one-way image rectifier compensating for the one-way image inversion introduced by the distal optical deflector; and a rotation device that is movable in a controlled manner by an outer ring, the rotating device rotating, simultaneously and synchronously about the optical axis, each of the distal deflector and the one-way image rectifier, wherein the proximal end of the endoscopic probe is coupled to the distal end of a cylindrical tube, each of the endoscopic probe and the cylindrical tube being rotatable with respect to the cylindrical handle, wherein the one-way image rectifier is arranged adjacent the proximal end of the cylindrical tube, and wherein the ocular lens is mounted in a cylindrical mount which is slidably and non-rotatably mounted in the median part of the cylindrical tube.

13. The rotary endoscope of claim 12, wherein the rotation device is arranged on a distal part of the cylindrical handle.

14. The rotary endoscope of claim 12, wherein the adjustment device surrounds the central part of the cylindrical handle and wherein rotation of the adjustment device causes a longitudinal displacement along the optical axis of the cylindrical mount.

15. The rotary endoscope of claim 12, further comprising:

a first mechanical connection device for transforming rotation movement of the adjustment device into longitudinal movement of a ring that surrounds the median part of the cylindrical tube; and a second mechanical connection device for transforming a movement of longitudinal translation of the ring surrounding the median part of the cylindrical tube into a longitudinal translation of the cylindrical mount.

16. The rotary endoscope of claim 15, wherein the ring surrounding the median part of the cylindrical tube comprises an inner annular groove which is adapted to receive a cylindrical finger.

17. The rotary endoscope of claim 12, wherein the cylindrical mount includes an outer radial finger which slidably engages a longitudinal slot arranged on the cylindrical tube.

18. The rotary endoscope of claim 12, further comprising at least one of:

the adjustment device comprising an inner helical thread which is adapted to engage a cylindrical finger; and the cylindrical tube including a mobile stop device which allows the endoscopic probe to rotate greater than 360°.

19. A rotary endoscope with a deflected distal sight, the endoscope comprising:

a cylindrical handle having a proximal part, a median part and a distal part;

an endoscopic probe comprising a lens, an optical image conveying system, a distal end, and a proximal end which extends from the distal end of the cylindrical handle;

an optical deflector arranged at the distal end of the endoscopic probe, the optical deflector introducing one-way inversion of an image of an object observed through a distal lateral lens port;

the endoscopic probe conveying the image of the object observed along an optical axis to an ocular lens;

an adjustment device comprising an outer ring which moves the ocular lens in a controlled manner, the ocular lens being disposed in a median part of the cylindrical handle and being movable longitudinally along the optical axis;

a one-way image rectifier arranged in the proximal part of the cylindrical handle, the one-way image rectifier compensating for the one-way image inversion introduced by the optical deflector; and a rotation device comprising an outer ring moving in a controlled manner, simultaneously and synchronously about the optical axis, each of the optical deflector and the one-way image rectifier, wherein each of the endoscopic probe and a cylindrical tube is rotatable with respect to the cylindrical handle, wherein the one-way image rectifier is arranged adjacent the proximal end of the cylindrical tube, and wherein the ocular lens is mounted in a cylindrical mount that is slidably and non-rotatably mounted in the median art of the cylindrical tube.

* * * * *